(12) United States Patent
Clark et al.

(10) Patent No.: US 12,383,254 B2
(45) Date of Patent: Aug. 12, 2025

(54) MULTI-COMPONENT ANCHOR SYSTEM AND METHODS

(71) Applicant: TIGON MEDICAL, Millersville, MD (US)

(72) Inventors: Jeremy Clark, Millersville, MD (US); Zac Sullivan, West Chester, PA (US); Greg Gasbarro, West Chester, PA (US)

(73) Assignee: Tigon Medical, Millersville, MD (US)

( * ) Notice: Subject to any disclaimer, the term of this patent is extended or adjusted under 35 U.S.C. 154(b) by 290 days.

(21) Appl. No.: 18/141,196

(22) Filed: Apr. 28, 2023

(65) Prior Publication Data

US 2023/0346364 A1 Nov. 2, 2023

Related U.S. Application Data

(60) Provisional application No. 63/336,209, filed on Apr. 28, 2022.

(51) Int. Cl.
*A61B 17/04* (2006.01)

(52) U.S. Cl.
CPC .. *A61B 17/0401* (2013.01); *A61B 2017/0409* (2013.01); *A61B 2017/044* (2013.01); *A61B 2017/0445* (2013.01)

(58) Field of Classification Search
CPC ........ A61B 17/0401; A61B 2017/0409; A61B 2017/044; A61B 2017/0445; A61B 2017/0414
See application file for complete search history.

(56) References Cited

U.S. PATENT DOCUMENTS

| 9,138,220 B2 * | 9/2015 | Hernandez | A61B 17/0401 |
| 2005/0283156 A1 * | 12/2005 | Schmieding | A61B 17/0401 606/329 |
| 2012/0150225 A1 * | 6/2012 | Burkhart | A61B 17/0401 606/232 |

* cited by examiner

*Primary Examiner* — Julian W Woo

(74) *Attorney, Agent, or Firm* — BRAINSPARK ASSOCIATES, LLC

(57) ABSTRACT

Systems, devices and methods for knotless fixation of tissue during a surgical procedure, including a multi-piece anchor having a separate distal anchor and cannulated proximal anchor component that are used to secure one or more sutures for surgical tissue repair without requiring suture knots. The distal body can include a closed aperture to allow insertion and/or free sliding of one or more suture strands. The multi-piece anchor is secured in a hole formed in bone by placing the distal anchor body in the hole and then advancing the proximal anchor component, such as a cannulated interference screw body, over a portion of the distal anchor body.

12 Claims, 20 Drawing Sheets

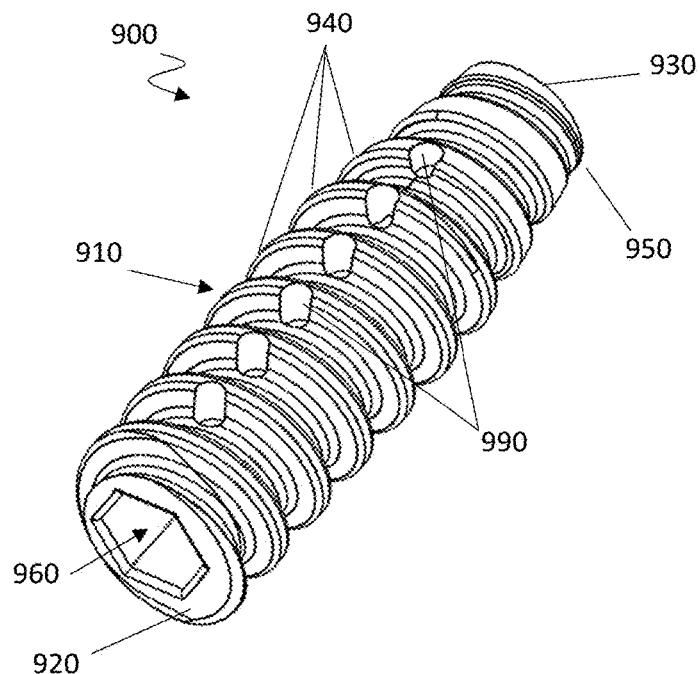
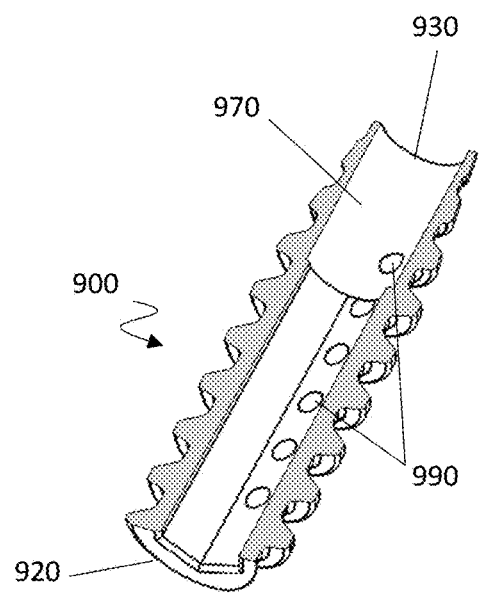
FIGURE 9A
FIGURE 9B
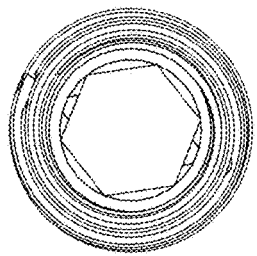
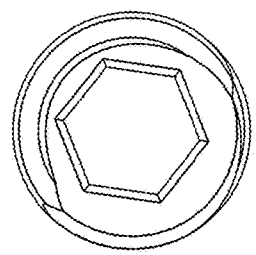
FIGURE 9C
FIGURE 9D

MULTI-COMPONENT ANCHOR SYSTEM AND METHODS

CROSS-REFERENCE TO RELATED APPLICATIONS

This application claims the benefit of U.S. Provisional Patent Application Ser. No. 63/336,209 entitled "DUAL ANCHOR," filed Apr. 28, 2022, the disclosure of which is incorporated by reference herein in its entirety.

TECHNICAL FIELD

The present application relates to anchors. More specifically, the present application relates to multi-component anchors used in medical procedures, such as rotator cuff repairs and/or other surgical procedures.

BACKGROUND OF THE INVENTION

When soft tissue separates and/or tears away from bone, surgical reattachment often becomes necessary. Various devices, including sutures, screws, staples, wedges, anchors and plugs have been used in the prior art to secure soft tissue to bone. Surgical methods utilizing suture anchors alone are disadvantageous for reattachment of large areas of detached tissue because they often do not allow good tissue to bone contact.

Reattachment of soft tissue to bone typically requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position. Also, the suture knots often are exposed to abrasion or cutting by sharp or rough areas along the walls of the bone canal into which anchors are typically inserted to provide fixation of tendon to bone.

Various knotless suture anchor systems have been developed which provide for attachment of suture and suture tapes to tissues and/or bone anchors within the use of knots, such as the knotless fixation system of U.S. Pat. No. 8,663,279 to Burkhart et al, the disclosure of which is incorporate herein by reference, but many of these prior art implants and their associated deployment tools are complex, difficult to operate, are relatively fragile and/or inflexible in their design or usage and/or tend to generate significant amounts of medical waste from disposable and/or non-reusable components of the system. Accordingly, a need exists for durable and improved knotless suture anchor systems and related surgical methods for attaching soft tissue to bone which do not require multiple suture knots and which utilize little or no disposable or non-reusable components.

BRIEF SUMMARY OF THE INVENTION

The instruments and methods of the present invention overcome many disadvantages of prior art systems and devices, such as those noted above, by providing a distal anchor body at a distal end of a surgical driver (which securely engages and locks with driver using a threaded or captured engagement system) with a cannulated proximal anchor body held on a less distal portion of the driver. In use, the distal anchor body and an attached suture are inserted into a bone opening, wherein rotation of the surgical driver releases the distal anchor body and concurrently rotates and advances the cannulated proximal anchor into the bone opening and over a portion of the distal anchor body to lock the suture in a desired manner. The device can then be removed from the patient and reloaded/reused with another anchor for easy reuse or disassembled and cleaned/sterilized for use in subsequent surgeries.

Other features and advantages of the present invention will become apparent from the following description of exemplary embodiments of the invention described with reference to the accompanying drawings.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 9A through 9D depict various views of one exemplary embodiment of a cannulated proximal anchor or screw;

DETAILED DESCRIPTION OF THE INVENTION

Embodiments of the invention are discussed in detail below. In describing embodiments, specific terminology is employed for the sake of clarity. However, the inventions are not intended to be limited to the specific terminology so selected. A person skilled in the relevant art would recognize that other equivalent parts can be employed and other methods developed without departing from the spirit and scope of the invention. All references cited herein are incorporated by reference as if each had been individually incorporated.

Various implementations of an anchor in accordance with the principles of the invention are described herein. The anchors may support two or more sutures and/or suture tapes and may be inserted into a patient's bone in a single series of steps.

Figure 1:
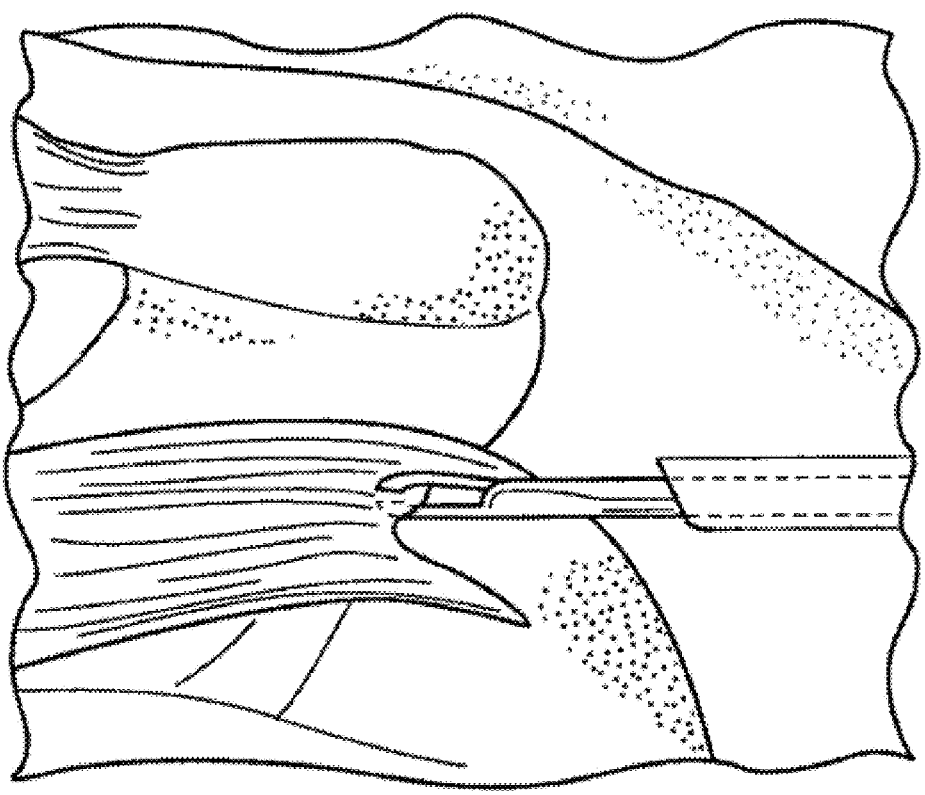
FIGS. 1 through 6 depict a series of steps of shoulder repair using a plurality of anchor devices according to the present invention.

FIG. 1 illustrates a side view of a human shoulder of a patient undergoing a rotator cuff repair in accordance with an exemplary embodiment of the present invention. Access to the subacromial space can be facilitated with a variety of cannulas in a known manner.

In various operations, a mobility of the tear can be assessed using, for example, a tissue grasper to determine whether a U or L-shaped component exists. Where large tears extend to the superior aspect of the glenoid, margin convergence suturing may be performed to reduce volume and strain on the repair. Subsequently, the length and width of the rotator cuff footprint may be assessed in a known manner and a bleeding bed for enhanced tendon to bone healing may be formed. This may be accomplished with a burr to perform a light dusting of the greater tuberosity, or by using a chondro pick to microfracture the footprint and maximize vascular channels.

Figure 2:
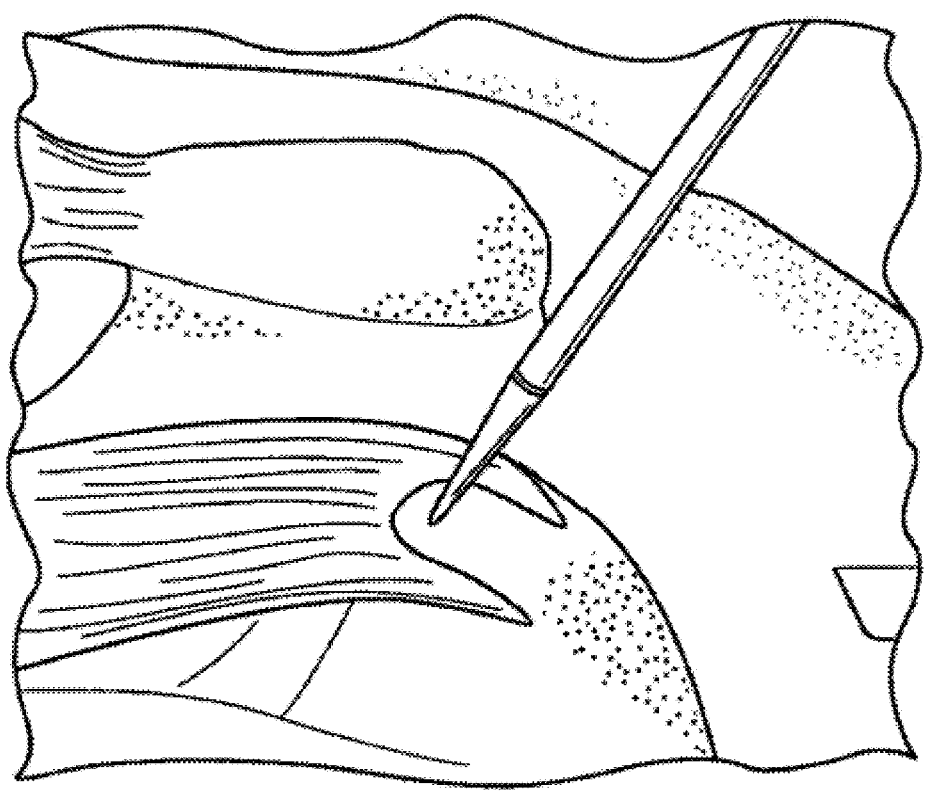
Figure 3:
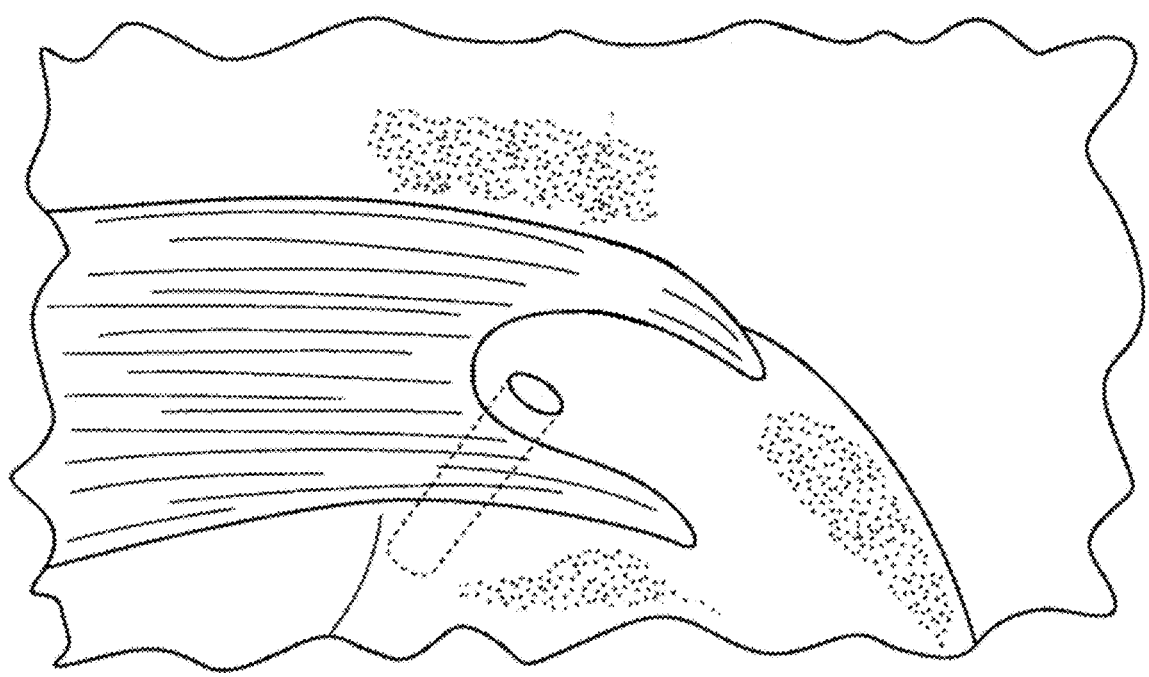

FIG. 2 illustrates the preparation of two pilot holes for two anchors that can be inserted in the medial row. A punch may be employed adjacent to the articular margin of the humerus and at about 45° angle to form a desired number of pilot holes or tunnels in the bone (e.g., two pilot holes).

Figure 4:
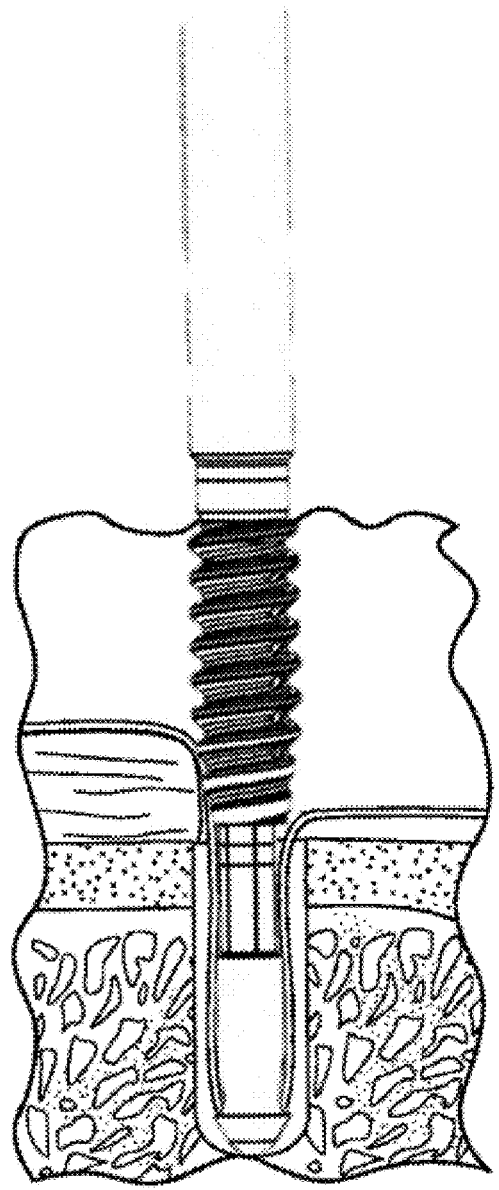

Subsequent to the formation of pilot holes, and as best shown in FIG. 4, a dual component anchor may be loaded onto a driver or deployment tool and one or more sutures may be placed through a distal opening of the anchor It should be understood that virtually any type of flexible material or suture may be utilized with the disclosed anchor components, and various other anchor embodiments may directly secure and/or hold tissues within the bone tunnel, if desired.

The distal tip of the driver is then inserted into a pilot hole, and the tool is then rotated to detach the distal anchor body from the tool while concurrently rotating and advancing a cannulated proximal anchor body into the pilot hole and over a proximal portion of the distal anchor body. Once the cannulated proximal anchor body is positioned at a desired location and orientation (e.g., flush with or recessed to the surface of the bone), the driver can be removed and the suture is secured. Desirably, the driver can then be reloaded with another dual component anchor and this process repeated for the other medial anchor.

Figure 5:
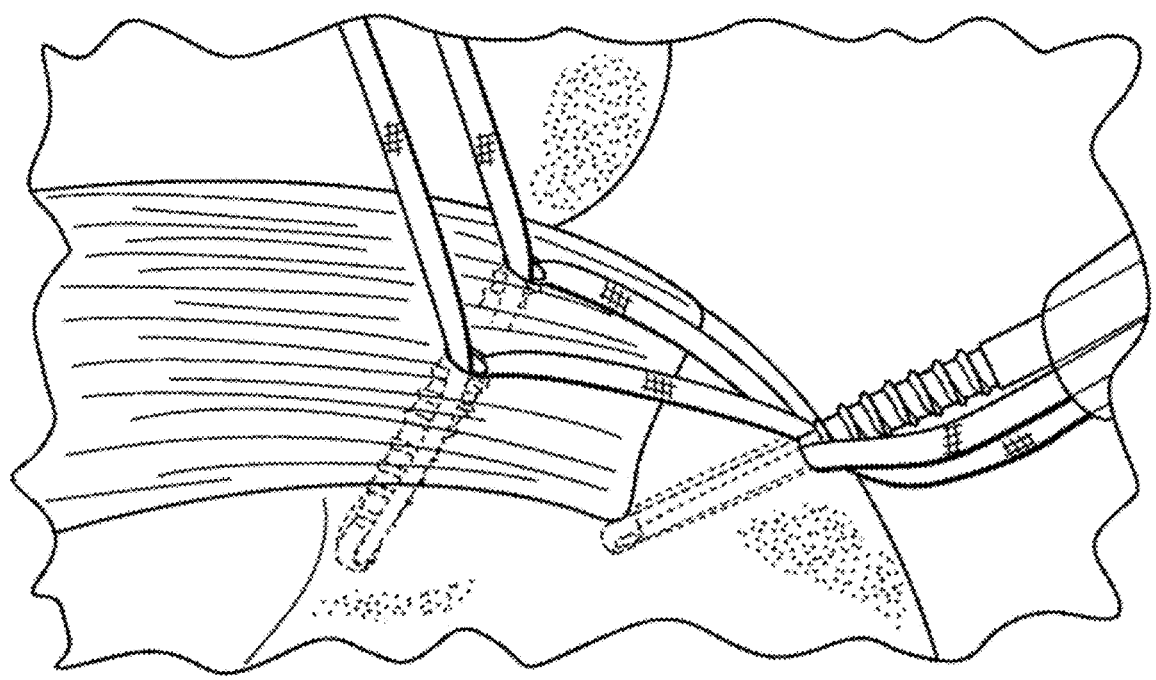
Figure 6:
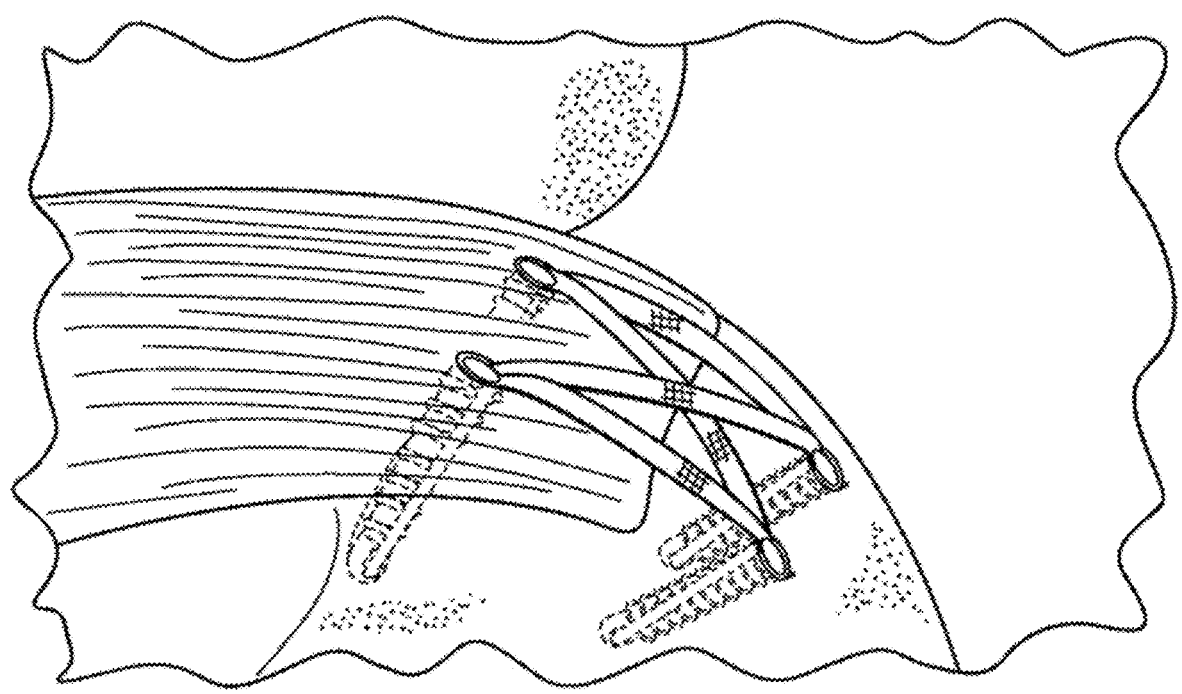

Referring to FIG. 5, one tail of suture tape from each medial anchor can be retrieved and loaded through the eyelet of another dual component anchor, and that implant is installed in then inserted into a preformed lateral bone socket. The tension of the suture tape(s) can be adjusted as necessary. This step can be repeated in another lateral bone socket with the other tails of suture tape from each medial anchor. The tails of the suture tape can then be cut to complete the construct as shown in FIG. 6.

Figure 7A:
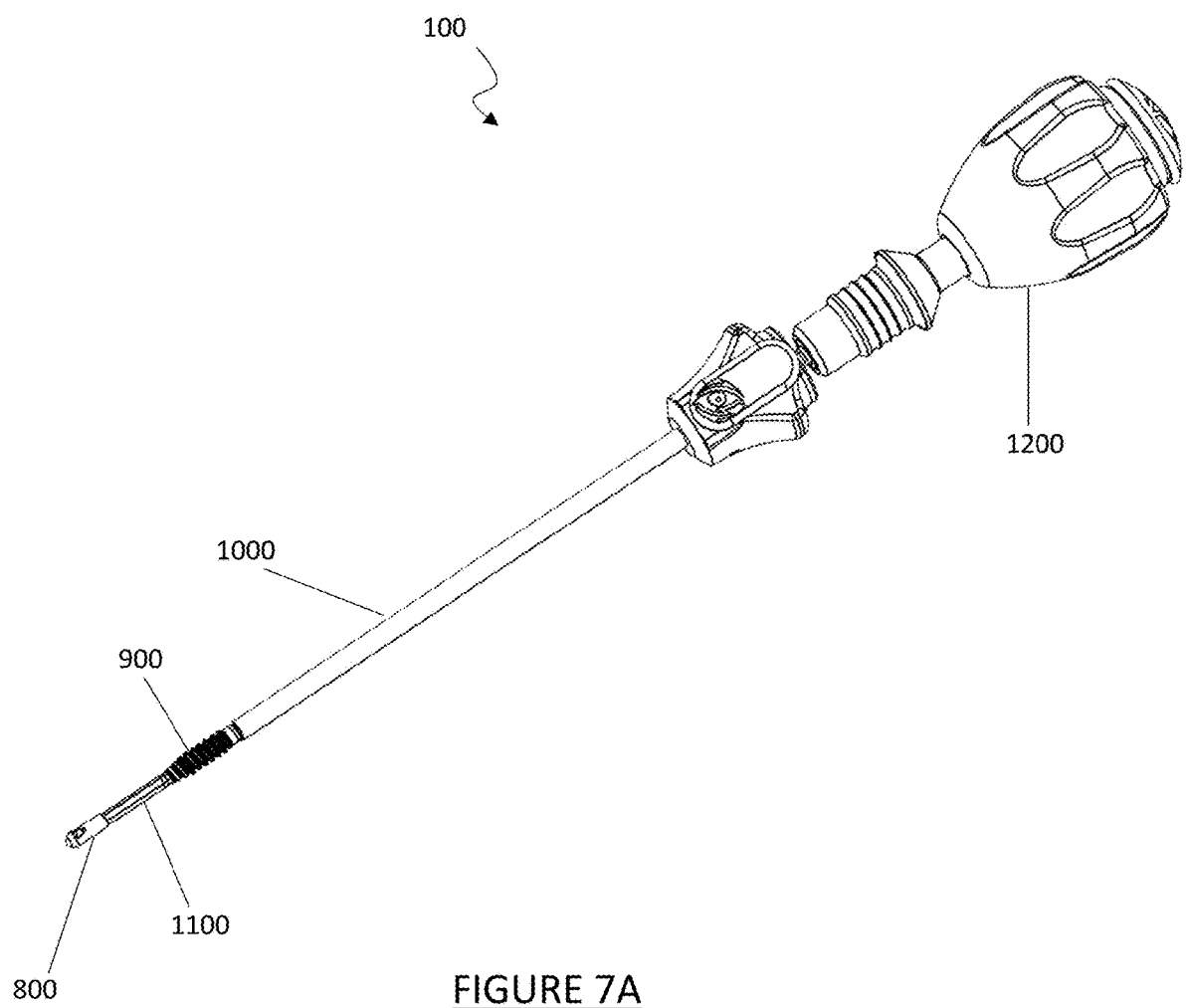
FIG. 7A depicts a perspective view of one exemplary embodiment of a multi-component anchor and associated surgical driver or deployment tool.
Figure 7B:
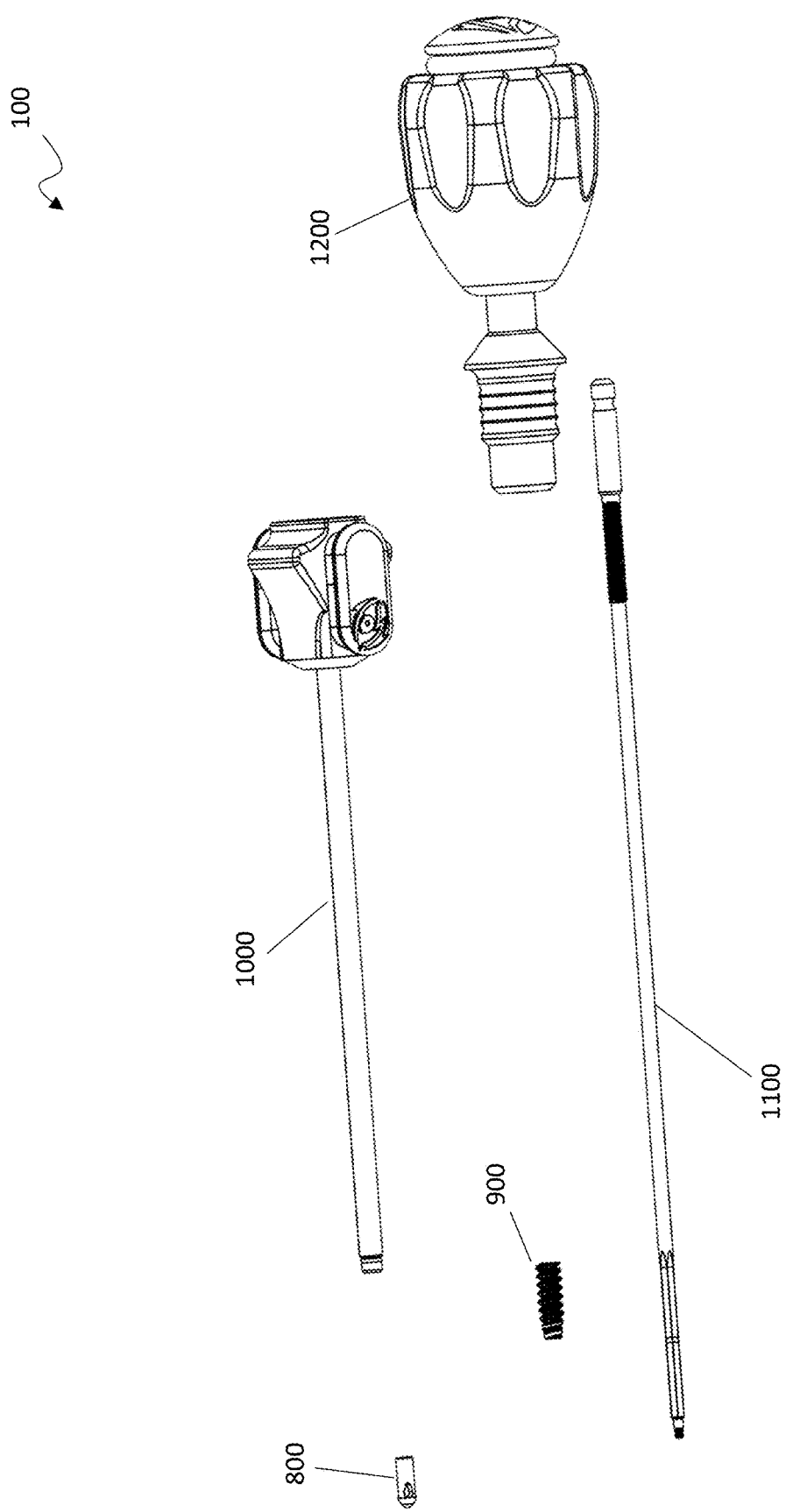
FIG. 7B depicts an exploded view of the individual components of the multi-component anchor and associated driver of FIG. 7A.
Figure 8A:
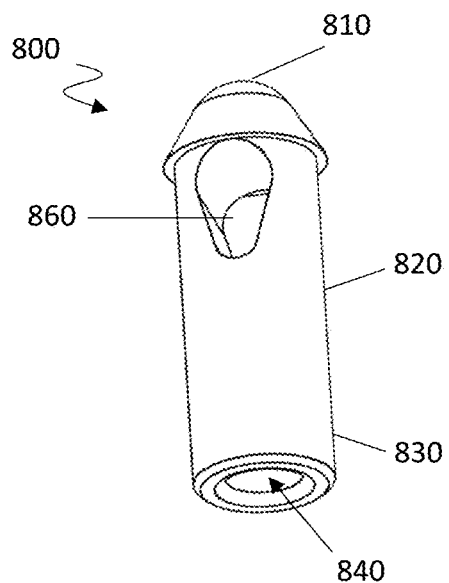
FIGS. 8A through 8D depict various views of one exemplary embodiment of a distal anchor for use with the various components disclosed herein.
Figure 8B:
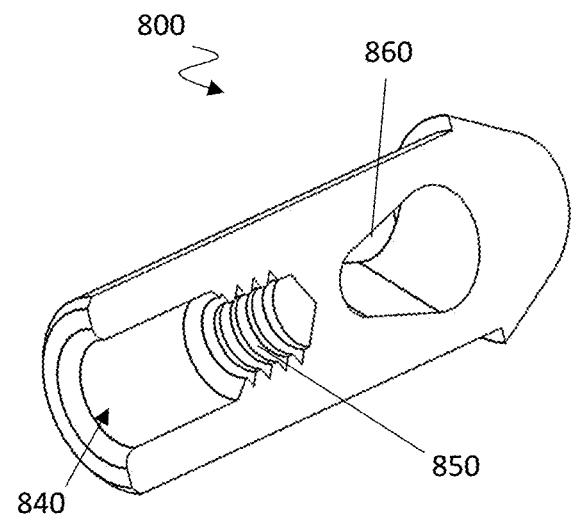
Figure 8C:
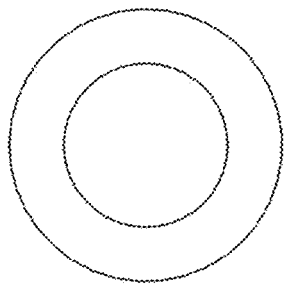
Figure 8D:
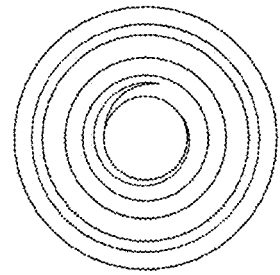

The various components of the dual component anchor and related instruments of the present invention are now described in greater detail. As shown in FIG. 7A (and with individual components shown in the exploded view of FIG. 7B), a driver 100 can be employed to hold and deploy the components of the dual component anchor to install the knotless fixation device. The driver 100 comprises an inner shaft 1100, a cannulated outer shaft 1000 and a handle or driver 1200. A cannulated proximal anchor body 900 is placed over the inner shaft 1100 and positioned at a distal end of the cannulated outer shaft 1000, and a distal anchor body 800 is positioned at a distal end of the inner shaft 1100.

FIGS. 8A through 8D depict various views of one exemplary embodiment of a distal anchor 800 for use with the various components disclosed herein. In this embodiment, the distal anchor 800 includes a domed tip 810, a central body 820, a shank section 830, an internal bore 840 and a threaded section 850 within the bore 840. As best seen in the cross-sectional view of FIG. 8B, an elongated generally transverse opening 860 is formed through the central body. This opening 860 will desirably allow for insertion of one or more sutures, tapes, or threads to extend through the suture opening and to the outer surface of the anchor components. The suture opening may accommodate one or more sutures, tapes, or threads. The suture opening may comprise a length and a width and may be of virtually any shape compatible with the underlying anchor component. The length and width may be selected to accommodate a suture, tape, or thread of desired size. The length and width may be selected to accommodate one or more sutures, tapes, or threads. Although only a single suture opening is depicted, it should be understood that a second suture opening may be located on the anchoring component, and any number of suture openings may be provided in any number of locations about the axis of the anchor.

Figure 18A:
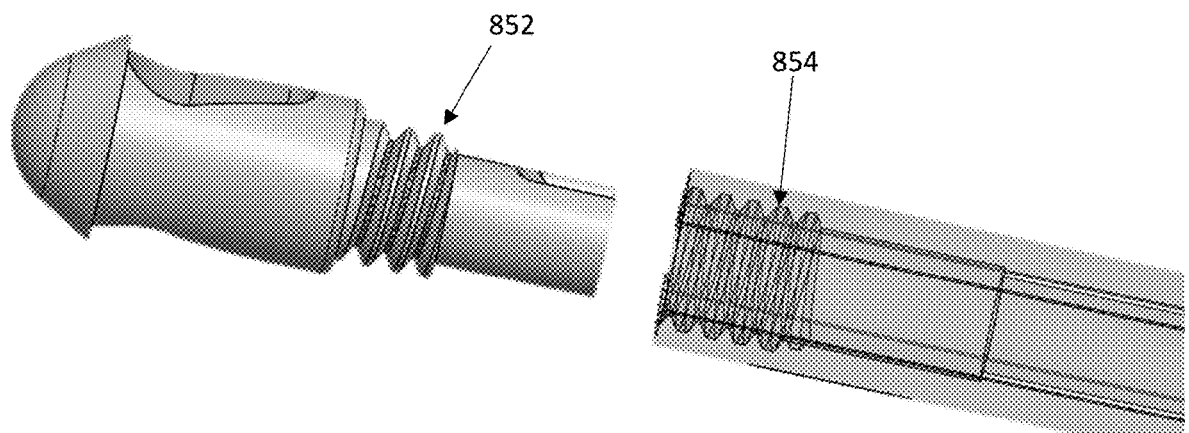
FIG. 18A depicts a threaded section of s distal anchor which engages with a corresponding inward facing thread on the distal tip of the inner shaft.

In various embodiments, the threaded section 850 of the distal anchor will desirably incorporate a male reverse or "left-handed" thread 852 (see FIG. 18A), which can desirably engage with a corresponding female inward facing thread 854 on the distal tip of the inner shaft 120. Desirably, the interaction between this pair of threads will desirably allow the distal anchor body to be strongly and/or rigidly secured to the inner shaft, yet allows the distal anchor 800 to be unthreaded and/or disengaged from the inner shaft 120 upon clockwise rotation of the inner shaft and associated proximal anchor 190 (where the bone will hold the distal anchor against rotation of the driver). This arrangement desirably allows the distal anchor 800 to be initially positioned within the bone tunnel and to remain stationary (e.g., to not rotate the anchor and/or suture within the tunnel) while the proximal anchor 190 is being rotated and advanced into the bone tunnel (as well as being advanced into engagement over the distal anchor 800).

In use, a suture or suture tape (not shown) can be inserted through the opening in the distal anchor 800, with the suture drawn tight and positioned along the combined shaft of the driver. The distal anchor 800 and distal end of the driver can be inserted into the bone tunnel in a generally known manner, and the surgeon can then hold the shaft handle of the cannulated outer shaft 1000 stationary while rotating the handle 1200 and attached inner shaft (preferably in a clockwise direction). Rotation of the inner shaft will be transmitted to the hexagonal shaft section 1170 of the inner shaft, which will rotate the associated proximal anchor 900 as it advances into the bone tunnel in a desired manner without rotating the distal anchor and/or the attached suture.

FIGS. 9A through 9D depict various views of a cannulated proximal anchor or screw 900. In this embodiment the proximal anchor 900 includes a central body 910 having a proximal end 920 and a distal end 930, with a series of externally facing screw threads 940 with a leading screw edge 950 and a longitudinally extending central bore 960. As best seen in the cross-sectional view of FIG. 9B, the central bore 960 includes a rounded bore section 970 located towards the distal end 920 and a hexagonal bore section 980 (or other driving shape) located towards the proximal end 930 of the anchor.

Desirably, the rounded bore section 970 is sized and configured to accommodate and/or engage with a shank section of a distal anchor body, as will be described later. In this embodiment, the proximal anchor 900 may also optionally include holes 990 for venting. The holes 990 may allow blood to travel through the proximal anchor 900 to facilitate fixation and/or bony ingrowth. The bore sections may similarly allow blood to flow through the anchor in a desired manner. The holes may be located along a longitudinal length of the anchor components. More or fewer holes may be provided than those depicted. Additional holes may be provided on surfaces 90 degrees, 180 degrees, and 270 degrees with respect to the view of FIGS. 9A and 9B. The holes provided on additional surfaces may be provided at the same or different longitudinal and radial locations. The cannulation of the proximal anchor and the vent holes will desirably allow for blood and biologic healing products to enter the anchor and facilitate healing. Bone may also in grow into the cannulation and vent holes to assist in healing. One may appreciate that this disclosed anchor system facilitates insertion and saves time and waste during the medical procedure.

In the disclosed embodiments, the various driver and/or other tool components such as the inner and outer shafts will desirably incorporate stainless steel components per ASTM F899. The shafts and/or other components of the driver that are used with the disclosed anchors will desirably be reprocessed and will be available sterile packed and attached to the anchor components and/or sutures.

Figure 10A:
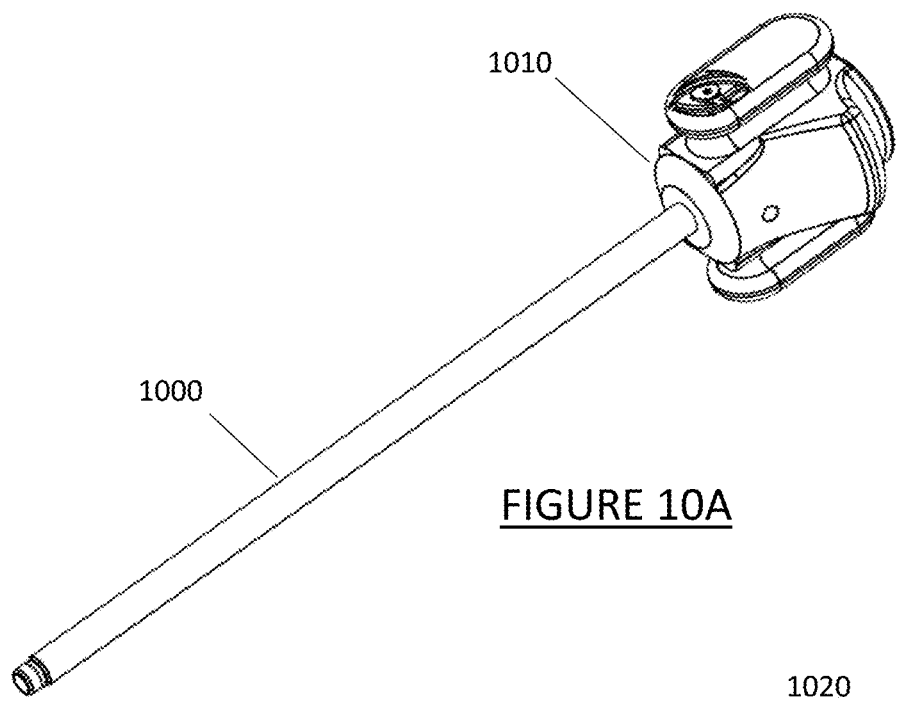
FIGS. 10A through 10D depict various views of one exemplary embodiment of a cannulated outer shaft and associated shaft handle.
Figure 10B:
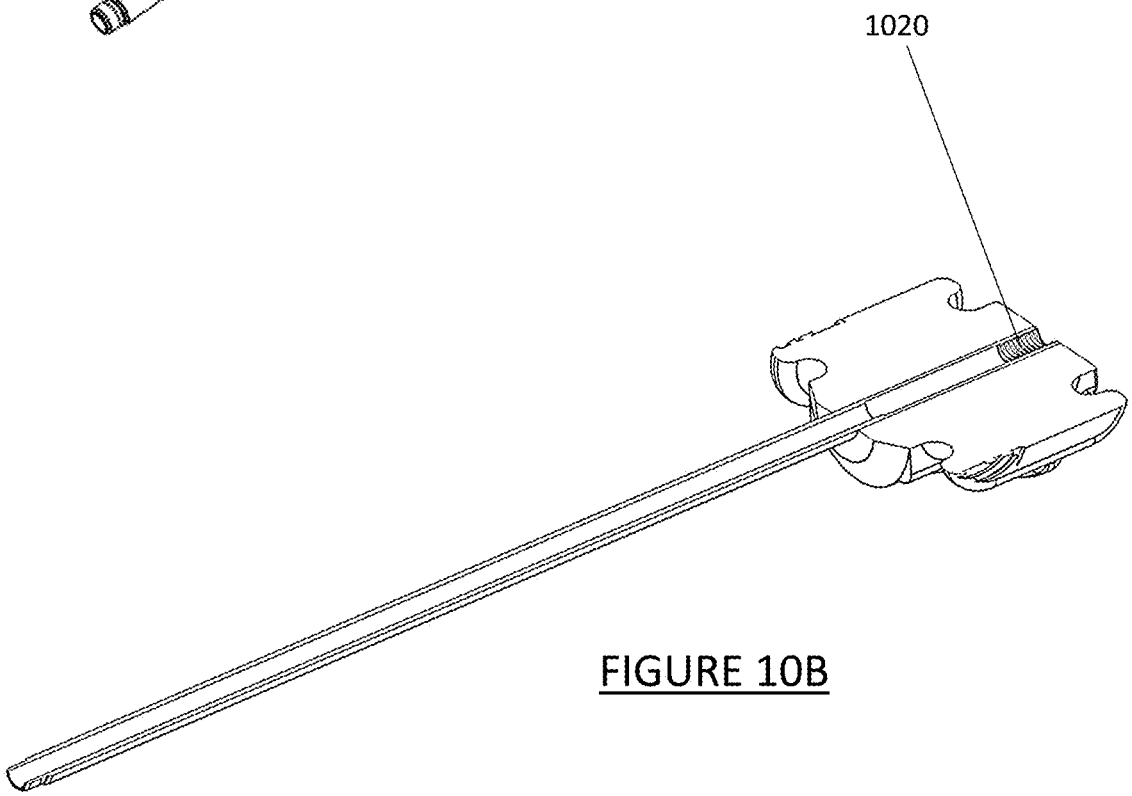
Figure 10C:
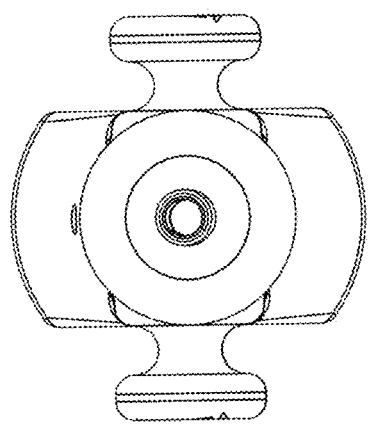
Figure 10D:
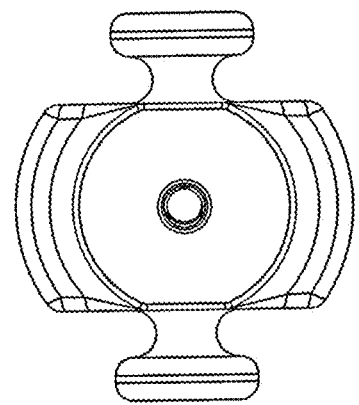
Figure 18B:
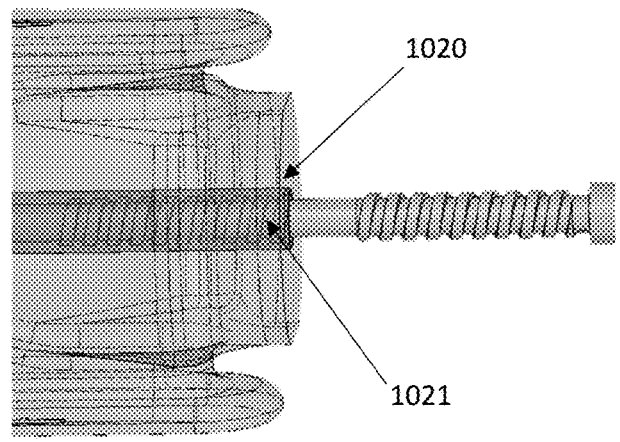
FIG. 18B depicts an internally threaded section formed at a proximal end of the handle which engages with an externally threaded section on a proximal portion of the inner shaft.

FIG. 10A depicts a cannulated outer shaft 1000 and associated shaft handle 1010. As best seen in FIG. 10B, the shaft handle is secured to the outer shaft, and a cannulation extends completely through the shaft and handle. An internally threaded section 1020 is desirably formed at a proximal end of the handle within the cannulation, with this female internally threaded section 1020 desirably engaging with a male externally threaded section 1021 on a proximal portion of the inner shaft (see FIGS. 11A and 18B). Desirably, the internally threaded section 1020 can be a left-hand thread, similar to the threaded section 1340 of the anchor body 1300.

Figures 11A, 11B:
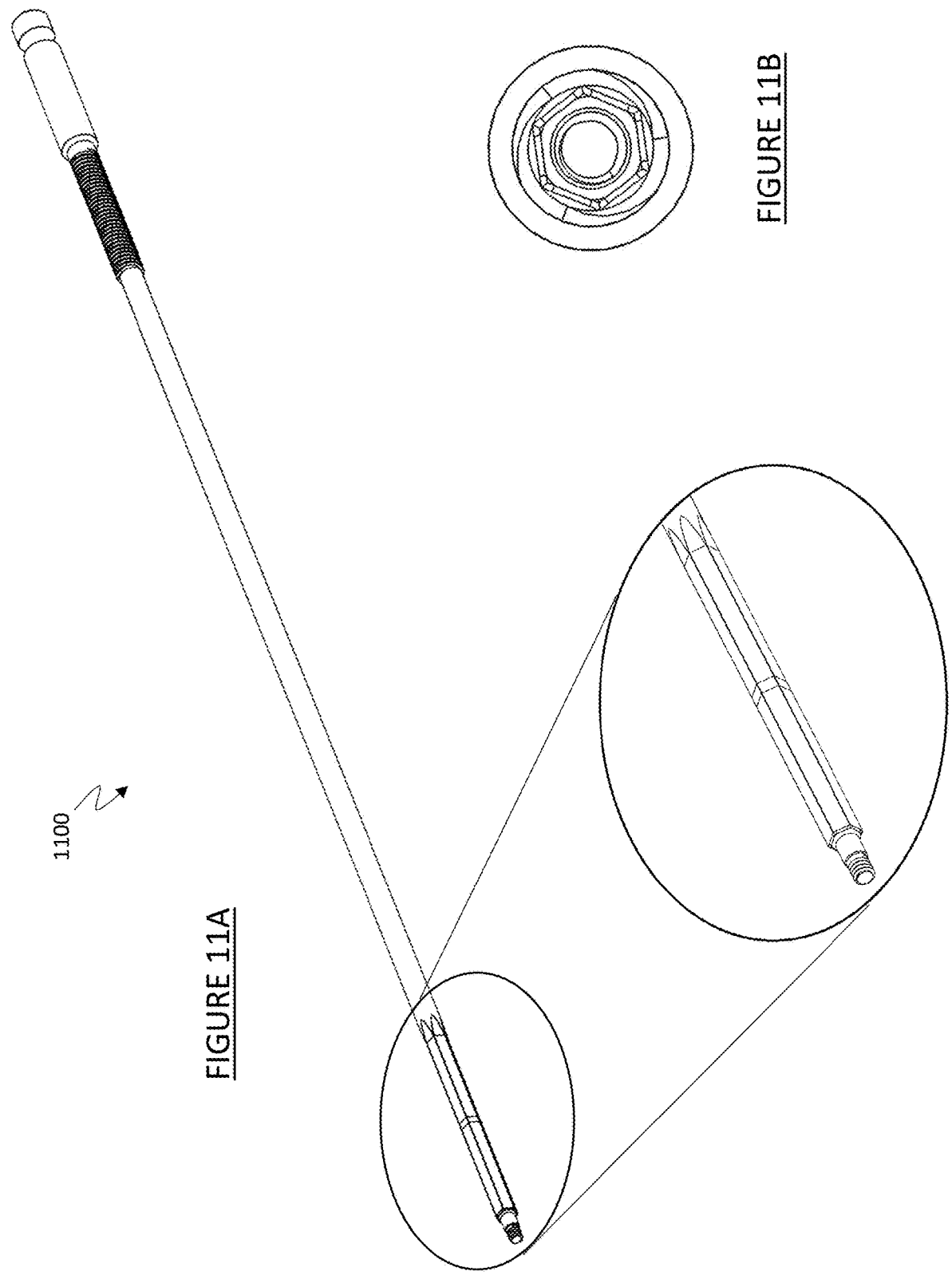
FIGS. 11A and 11B depict views of one exemplary embodiment of an inner shaft.

FIG. 11A depicts a perspective view of an inner shaft 1100. The inner shaft 1100 desirably incorporates a solid shaft body 1110 having a proximal shaft end 1120 and a distal shaft end 1130. An AO-type fitting or similar modular connector 1140 is positioned at the proximal end 1120, with an externally threaded inner shaft portion 1150 formed near the proximal end 1120. The inner shaft 1100 further includes a distal threaded section 1160 at the distal shaft end 130, with a hexagonal shaft section 1170 formed near the distal shaft end.

Figure 12:
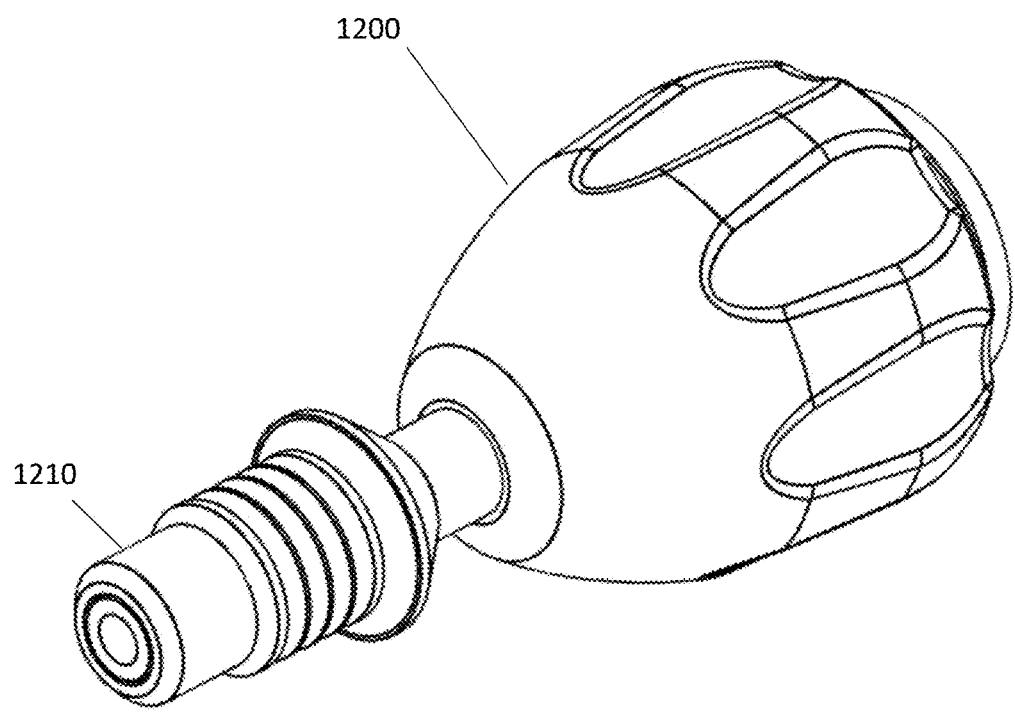
FIG. 12 depicts a perspective view of one exemplary embodiment of a handle with an AO-type fitting or similar modular attachment.

In use, the inner shaft 1100 can be inserted into the cannulated outer shaft 1000, with the internally threaded section 1020 of the cannulated outer shaft 1000 desirably engaged with at least a few threads of the externally threaded inner shaft portion 1150, such that the ends of the inner shaft 1100 extend from both of the proximal and distal ends of the cannulated outer shaft 1000 and shaft handle 1010. A cannulated proximal anchor body 900 is inserted over the distal tip of the inner shaft 1100, and engaged with and slid down the hexagonal shaft section 1170 of the inner shaft 110 until it is seated against the distal tip of the outer shaft 1000 (where it can be retained by a taper or press-fit arrangement between the inner surfaces of the screw and the outer surfaces of the inner shaft, or similar arrangements). A distal anchor body 1300 can then be securely threaded onto the distal shaft end 1130 of the inner shaft 1100, and a handle 1200 with an AO-type fitting or similar modular attachment 1210 (see FIG. 12) can be secured to the proximal end of the inner shaft. The multi-component anchor and associates driver are now ready to be loaded with suture and utilized during a surgical procedure.

In this embodiment, the handle 1200 desirably includes a quick-connect interface, such as the AO quick connect interface disclosed in U.S. Pat. No. 9,447,803B1, the disclosure of which is incorporated herein by reference. Desirably the interface (or other connection and/or "chuck" types well known in the art) will allow the handle to accommodate a variety of surgical tools, including ratcheting adapters, torque limiters and/or multipliers, counter torque wrenches, awls, punches, trephines and/or the like.

Figure 13A:
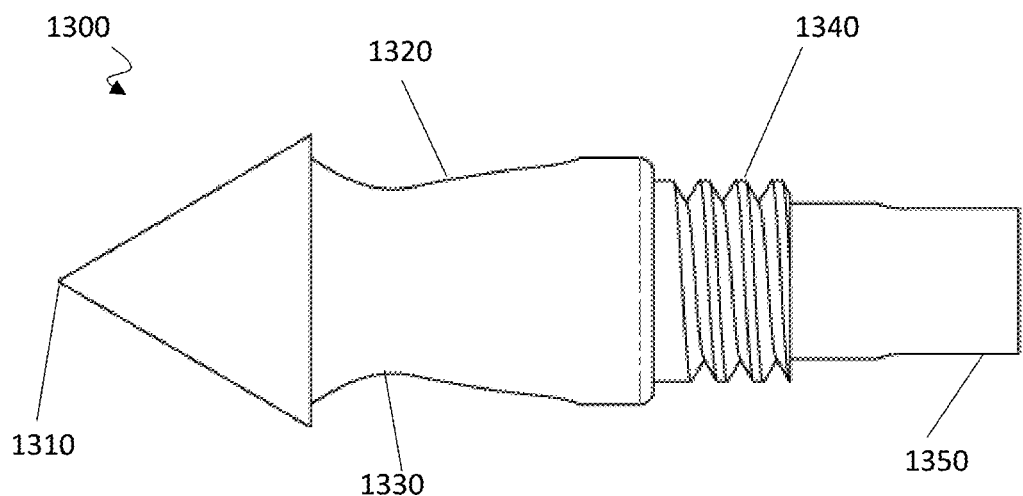
FIGS. 13A and 13B depict views of an alternative embodiment of a distal anchor for use with the various components disclosed herein.

FIG. 13A depicts an alternative embodiment of a distal anchor body 1300 for use with the various components disclosed herein. In this embodiment, the anchor body 1300 includes a pointed tip 1310, a central body 1320 having a necked section 1330, a threaded section 1340 and a shank 1350. In various embodiments, the tip 1310 can facilitate insertion of the implant into the targeted bone and/or preformed hole therein.

Figure 13B:
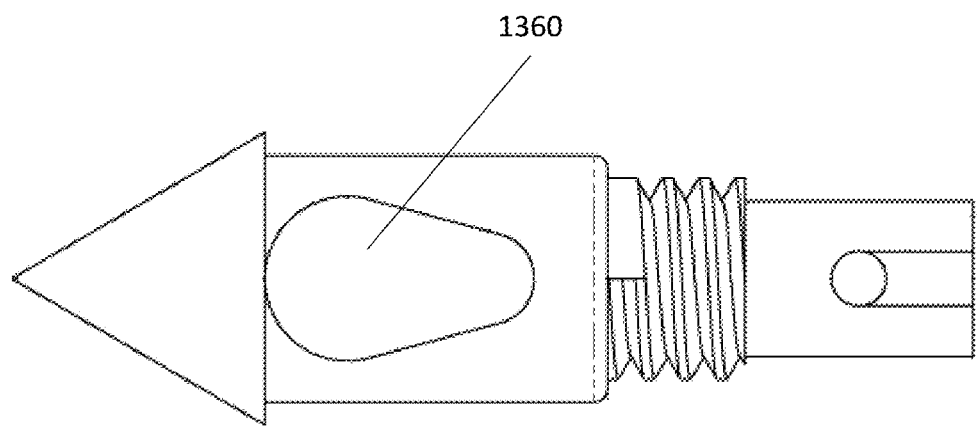
Figure 14A:
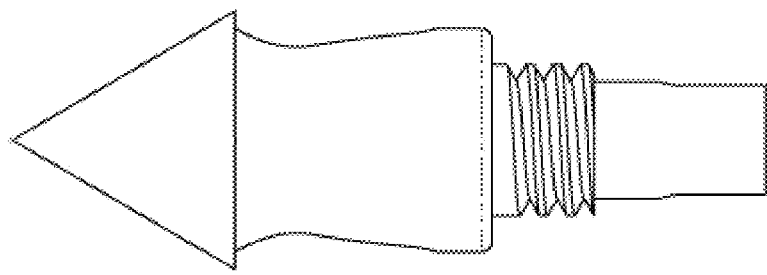
FIGS. 14A and 14B depict views of another alternative embodiment of a distal anchor for use with the various components disclosed herein.
Figure 14B:
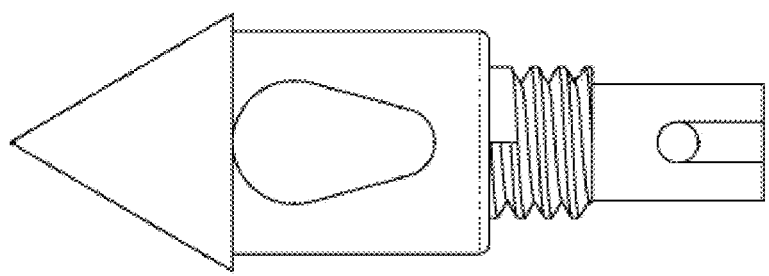
Figure 15A:
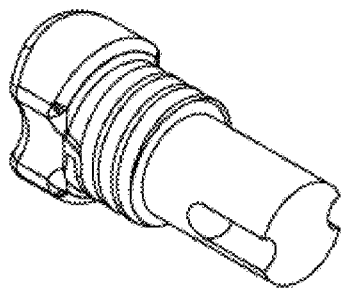
FIGS. 15A through 15C depict views of another alternative embodiment of a distal anchor for use with the various components disclosed herein.
Figure 15B:
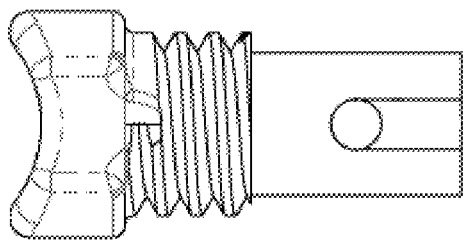
Figure 15C:
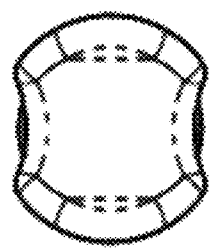
Figure 16A:
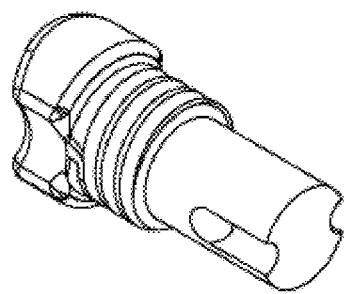
FIGS. 16A through 16C depict views of another alternative embodiment of a distal anchor for use with the various components disclosed herein.
Figure 16B:
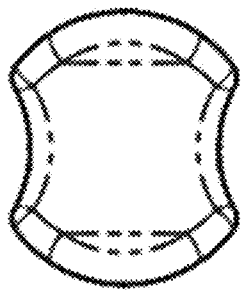
Figure 16C:
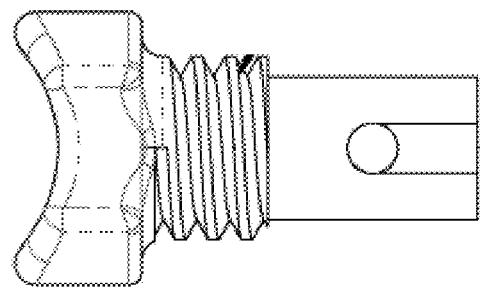
Figure 17A:
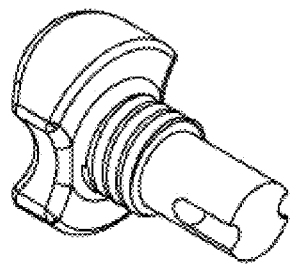
FIGS. 17A through 17C depict views of another alternative embodiment of a distal anchor for use with the various components disclosed herein.
Figure 17B:
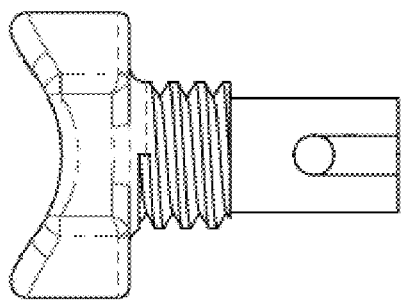
Figure 17C:
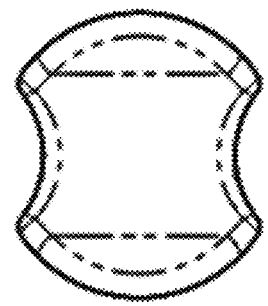

As best seen in FIG. 13B, an elongated generally transverse opening 1360 is formed through the central body, with a smaller through hole 1370 formed through the shank 1350. The opening 1360 will desirably allow for insertion of a suture, tape, or thread to extend through the suture opening and to the outer surface of the anchor components. The suture opening may accommodate one or more sutures, tapes, or threads. The suture opening may comprise a length and a width and may be of virtually any shape compatible with the underlying anchor component. The length and width may be selected to accommodate a suture, tape, or thread of desired size. The length and width may be selected to accommodate one or more sutures, tapes, or threads. Although only a single suture opening is depicted, it should be understood that a second suture opening may be located on the anchoring component, and any number of suture openings may be provided in any number of locations about the axis of the anchor.

If desired, a suture opening can be formed in an oval and/or oblate spheroid shape, which desirably allows room for multiple suture tapes to be loaded and/or "stacked" into a single opening without compressing, twisting, wrinkling, stretching and/or otherwise compromising the tape. In at least one exemplary embodiment, a proximal inner surface of the opening can incorporate at least one flattened and/or less curved inwardly-facing section, which desirably facilitates the accommodate of a plurality of surgical tapes by the opening.

In various embodiments, the conical configuration of the tip can facilitate self-punching of the anchor, if desired. The conical configuration of the tip may also facilitate anchor fixation, as well as potentially accelerated graft/tendon healing to bone.

The anchor may comprise any material, for example, polyether ether ketone (PEEK). The threaded portion and/or the tip portion of the distal anchor component may comprise the same or different materials. For example, the threaded portion(s) and/or tip portion may comprise PEEK. Alternatively, the threaded portion may comprise PEEK and the tip portion may comprise metal. The metal may be any metal known to one skilled in the art. The material may be selected based on the strength of the bone or tissue into which the anchor is being inserted.

In various embodiments, the driver desirably incorporates two sets of male left-hand threads that provide for unique loading and deploying of the implant components during surgery. The first set of threads is located on the distal end of the inserter and distal anchor, and these threads enable the distal anchor body to be easily loaded and secured to the inner shaft during preparation on the back table intraoperatively. The second set of threads is located near the proximal ends of the inner and outer shafts of the inserter (although other cooperating locations on the shafts could be utilized in a similar manner) and these threads facilitate the deployment of the cannulated proximal anchor once the distal anchor has been positioned at the desired fixation location. The combination of both left-hand thread sets desirably ensures a controlled, simultaneous, and mechanical deployment of the distal and proximal anchors, which prevents suture tangling and allows for smooth sliding of the sutures within the distal eyelet. Moreover, the incorporation of these design elements creates a more robust and environmentally friendly reusable product.

Unlike other anchor system which may utilize a tension suture or similar arrangement to retain anchor components on a deployment tool, the present system utilizes cooperating threads on an outer surface of the inner shaft and an inner surface of the distal anchor to rigidly secure the distal anchor to the driver to create a very robust construct. Not only is the solid inner shaft significantly stronger and/or more rigid than currently available anchor systems (which commonly use cannulated inner shafts in their deployment tools), but the female engagement threads within the shank of the distal anchor dramatically increases the strength and durability of the distal anchor during initial placement in the bone tunnel, and can prevent the distal anchor component from breaking and/or displacing if a common surgeon error is made such as inserting the anchor at an incorrect trajectory and/or mistakenly hammering the anchor into bone rather than into the prepared pilot hole. Moreover, the flattened distal surface of the solid inner shaft, which can engage directly against a corresponding flattened surface within the distal anchor (e.g., at the end of the threaded opening) will desirably transmit forces directly to the distal anchor without stressing the threaded engagement therebetween, which can provide for self-tapping of the anchor (e.g., where a metal tipped anchor component may be employed). Such rigid engagement allows the surgeon to optionally remove and/or reinsert a distal anchor in a bone tunnel prior to proximal anchor deployment, and can even allow the surgeon to redirect the bone tunnel trajectory at the surgeon's option.

In various embodiments, the threaded section 1340 of the anchor body 1300 will desirably incorporate reverse or "left-handed" thread, which can desirably engage with a corresponding inward facing thread on the distal tip of the inner shaft 120. This pair of threads are desirably adapted and configured to unthread or disengage the distal anchor body 1300 from the inner shaft 120 upon clockwise rotation of the inner shaft and associated cannulated proximal anchor body 190. Desirably, when the distal anchor body contacts the bone tunnel, friction and normal forces on the distal anchor body inhibit rotation of this component, while the tool is rotated and the inserter shaft spins clockwise, releasing the distal anchor component instead of capturing it because of the left-hand thread on the anchor and driver. This forces the distal anchor downwards generating normal forces preventing additional rotation of the distal anchor. Desirably, the distal anchor body 1300 positioned within the bone tunnel will remain stationary (e.g., not rotate the anchor and/or suture therein) while the cannulated proximal anchor body 190 is being rotated and advanced into the bone tunnel as well as being advanced into engagement over the distal anchor body 1300. In addition, a gap created by the rib of the distal anchor desirably allows suture to slide within the pilot hole in the bone despite axial forces and/or narrowing of the pilot hole.

In use, a suture or suture tape (not shown) can be inserted through the opening in the distal anchor body 1300, with the suture drawn tight and positioned along the combined shaft of the deployment tool. The distal anchor body 1300 and distal end of the deployment tool can be inserted into the bone tunnel in the known manner, and the surgeon can then hold the shaft handle of the cannulated outer shaft 1000 stationary while rotating the handle 1200 and attached inner shaft. Rotation of the inner shaft will be transmitted to the hexagonal shaft section 1170 of the inner shaft, which will rotate the associated cannulated screw 900 as it advances into the bone tunnel.

Desirably, rotation of the inner shaft relative to the stationary outer shaft 1000 will cause the internally threaded section 1020 of the cannulated outer shaft 1000 to advance distally relative to externally threaded inner shaft portion 1150, thereby a longitudinal urging force against the cannulated screw 900 to assist with entry and passage into the bone tunnel as the clockwise rotation advances the outer shaft and cannulated anchor downwards because of the left hand threads located at the proximal end of the inserter. Concurrently, the left-hand thread arrangement between the distal anchor body 1300 and the inner shaft will desirably unthread the distal anchor body 1300 (which is engaged with the surround bone of the bone tunnel) from the inner shaft, thereby inhibiting the distal anchor body 1300 from rotating in an unwanted manner as the cannulated screw 900 is rotated and advanced into the bone tunnel. Once the cannulated screw has been fully inserted into the bone tunnel (which may be flush with the bone and/or recessed relative to the bone surface, as desired by the surgeon), the cannulated screw 900 will desirably be fully engaged with the distal anchor body 1300 and the suture extending therefrom, and the deployment tool can be removed from the anchoring components. The deployment tool can then be desirably reused for additional anchor deployment in the same surgical precure and/or retained and re-sterilized for subsequent surgical procedures.

In one exemplary embodiment, a surgical procedure utilizing the disclosed multi-component anchors can include the following steps:

(1) Capture the soft tissue necessary for repair;
(2) Use a Tapered Awl (e.g., 3.5 mm) to create a hole in the desired implant location, using laser lines as reference for depth;
(3) Insert the inner shaft into the round quick connect handle;

(4) Slide the cannulated outer shaft over the inner shaft and screw until fully seated;
(5) Place a proximal anchor of desired size onto the inner shaft and slide proximally until fully seated;
(6) Place the distal anchor of desired type and size (e.g., sharp or blunt) onto the distal end of the inner shaft;
(7) Pass suture through the distal eyelet of the device. Insert the anchors into the hole created by the Tapered Awl until the distal tip is at the base of the hole;
(8) Pull suture to create desired tension while providing counterforce on the handle to keep anchors inside the hole.
(9) While continuing to place pressure into the hole and holding the outer inserter stationary, rotate the round quick connect handle to screw the proximal anchor into the bone hole until the anchor is buried flush. A laser line on the inserter will allow for a 2 mm countersink if desired; and
(10) remove inserter and cut excess suture as desired.

In another exemplary embodiment, a surgical procedure utilizing the disclosed multi-component anchors can include the following steps:
(1) Capture the soft tissue necessary for repair;
(2) Prepare the tendon using preferred stitching technique;
(3) Use a tendon measurement block to measure the tendon and determine the size of tenodesis screw;
(4) Use a guide pin to create a hole in the desired tenodesis screw location, using laser lines as reference for depth;
(5) Leave the guide pin in the hole in the bone and disconnect the proximal end of the guide pin from the drill;
(6) Connect the appropriately sized reamer to the drill and slide the cannula of the reamer over the placed guide pin;
(7) Enlarge the hole created by the guide pin using the cannulated reamer to desired depth using laser lines as reference;
(8) Remove both reamer and guide pin from the bone.
(9) Select outer and inner inserters of appropriate length and diameter;
(10) Connect Inner inserter to quick connect handle and insert inner inserter into outer inserter. Screw outer inserter onto inner inserter;
(11) Place anchor on the distal tip of the inner insert and insert nitinol loop through inserter so the loop is at the tip of the anchor;
(12) Insert suture on tendon through nitinol lasso loop and pull suture until the end of the tendon is at the tip of the anchor; and
(13) Pull tendon into hole while screwing in anchor by holding the outer inserter steady and twisting the quick connect handle clockwise.

FIGS. 14A, 14B, 15A through 15C, 16A through 16C and 17A through 17C depict various additional distal anchor body configurations which can be utilized in a similar manner with the disclosed deployment tool. In some embodiments, a surgical kit containing a variety of different distal anchor body implant components can be provided, which may optionally include a series of cannulated screws of the same or differing shapes and/or sizes. Depending upon the surgical need and surgeon preference, among other factors, a surgeon will desirably be able to select a desired distal anchor body implant and appropriate cannulated screw from the surgical kit and utilize the deployment device with the surgeon's chosen suture or tape, which can be loaded on the distal anchor body implant at any point prior to and/or during the surgical procedure. In some embodiments, a plurality of anchors can be sequentially deployed using a single reusable deployment tool, which greatly reduced surgical waste while increasing flexibility of the system.

Various embodiments can include a driver with a kit of distal anchors having variable tip geometries, so that the surgeon can choose the best style intraoperatively. The design of these tips will desirably include the previously disclosed male inner shaft into female recess on the distal anchor, which can allow various different tip configurations to be used with a single driving tool.

The disclosed deployment tool is desirably simple and easy to disassemble, clean and sterilize (and/or re-sterilize) using standard cleaning and sterilization equipment (e.g., steam autoclaves or similar devices) commonly available at hospitals and/or medical centers.

The knotless fixation device of the present invention advantageously minimizes or eliminates the need to tie knots. The use of such a multi-component anchor also provides secure fixation of the suture construct—the secure suture construct results from the suture being pushed into a hole and held tightly by the anchoring components.

In the preferred embodiment of the present invention, as mentioned above, suture and/or suture tape can be used with the anchor to fix tissue to bone. However, the anchor of the present invention can be used with any type of flexible material or suture. In another preferred embodiment, an allograft or biological component may be used instead of suture or tape. The allograft or biological component may be comprised of tendon or pericardium, for example, which provides improved tissue repair. In yet additional embodiments, any combination of suture, suture tape, and allograft or biological component may be employed, depending on the characteristics of the specific surgical repair and/or as desired.

The disclosed embodiments allow the disclosed anchor components to be provided in a non-preloaded condition, if desired, such that the surgeon has the intraoperative flexibility to choose an appropriate anchor configuration and load whatever suture or tape the surgeon feels is best for the surgery into the anchor. There are many different surgeon preferences for tapes and/or sutures, as well as the potential need for different colors, sizes and/or styles of tape in a single surgery. The disclosed embodiments desirably allow an anchor to be utilized with any style, color and/or size of surgical suture and/or tape, which allows the surgeon to customize their anchor for whatever type of repair he or she needs.

Desirably, individual components of the anchor can be available for purchase and provided in a sterile condition, such as a package containing a single distal anchor component and an associated cannulated proximal anchor component. Such anchor components can be opened and/or prepared at a back table during the surgical procedure, and mated with the pre-sterilized driver as necessary during the surgical procedure.

Desirably, the suture openings on the anchor are sized and configured to accommodate three or more suture tapes within a single hole, which in various embodiments can allow 6 or more suture tapes to be utilized with a single anchor (i.e., where the anchor incorporates two suture holes). This is a significant improvement on many existing anchor designs, which may only accommodate a single tape in a single anchor hole and/or no more than two suture tapes to anchor (i.e., where the anchor incorporates two suture holes).

Although the present invention has been described in relation to particular embodiments thereof, many other variations and modifications and other uses will become apparent to those skilled in the art. It is preferred, therefore, that the present invention be limited not by the specific disclosure herein. Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

Note that, in various alternative embodiments, variations in the position and/or relationships between the various figures and/or modular components are contemplated, such that different relative positions of the various modules and/or component parts, depending upon specific module design and/or interchangeability, may be possible. In other words, different relative adjustment positions of the various components may be accomplished via adjustment in separation and/or surface angulation of one of more of the components to achieve a variety of resulting implant shapes and/or sizes, thereby accommodating virtually any expected anatomical variation.

Of course, method(s) for manufacturing the anchors and driving tools and implanting the devices into bone are contemplated and are part of the scope of the present application.

While embodiments and applications of the present subject matter have been shown and described, it would be apparent to those skilled in the art that many more modifications are possible without departing from the inventive concepts herein. The subject matter, therefore, is not to be restricted except in the spirit of the appended claims.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of knotless tissue fixation comprising:
providing a suture;
securing the suture to tissue to be fixated;
preloading a cannulated proximal anchor component on a shaft of a driver;
preloading a distal anchor component on the shaft of the driver, the distal anchor component being separated from the cannulated proximal anchor by a spacing;
capturing the suture attached to the tissue with the distal anchor component, the distal anchor component threaded onto and rigidly fixed to a first externally threaded region of the shaft;
inserting the distal anchor component and the captured suture into bone; and
rotating the shaft to rotate and advance the proximal anchor component into the bone while concurrently unthreading the distal anchor component from the first externally threaded region of the shaft, thereby securing the suture and providing tissue fixation without tying any knots in the suture.

2. The method of claim 1, wherein the cannulated proximal anchor component is an interference screw.

3. The method of claim 1, wherein the shaft of the driver comprises a solid inner rod assembly which extends through a cannulated outer shaft assembly, the solid inner rod assembly having a second externally threaded region of the shaft that is longitudinally spaced apart from the first externally threaded region of the shaft, the cannulated outer shaft assembly having an inwardly facing threaded region which engages and disengages with the second externally threaded region of the shaft.

4. The method of claim 3, wherein the solid inner rod assembly further includes a driving region positioned between the first externally threaded region and the second externally threaded region of the shaft, the driving region having a non-circular cross-section.

5. The method of claim 4, wherein the cannulated proximal anchor component is positioned over and rotatably linked to the driving region.

6. The method of claim 5, wherein the inner surface of the cannulated proximal anchor component can slide longitudinally relative to the driving region of the solid inner rod.

7. The method of claim 6, wherein the inner surface of the cannulated proximal anchor has a hexagonal inner surface for receiving a corresponding outer surface of the driving region.

8. The method of claim 3, wherein the proximal anchor component is rotated and advanced by holding a handle of the cannulated outer shaft assembly such that the proximal anchor component rotates relative to the distal anchor component.

9. The method of claim 1, wherein the first externally threaded region of the shaft is positioned adjacent a distal end of the shaft.

10. The method of claim 1, wherein the first externally threaded region comprises a left-handed threaded region.

11. The method of claim 1, wherein rotation of the shaft in a clockwise direction rotates and advances the proximal anchor component into the bone while concurrently unthreading the distal anchor component from the first externally threaded region of the shaft.

12. The method of claim 1, wherein a distal end of the shaft comprises a flattened surface, and the flattened surface abuts a corresponding flattened inner surface of the distal anchor component when the distal anchor component is preloaded on the shaft of the driver.

\* \* \* \* \*